United States Patent
Wu et al.

(10) Patent No.: US 9,658,203 B2
(45) Date of Patent: May 23, 2017

(54) METAL COLLECTION SOLUTION AND METHOD OF ANALYZING SUBSTRATE CONTAMINATION

(71) Applicant: Kabushiki Kaisha Toshiba, Minato-ku (JP)

(72) Inventors: Jiahong Wu, Yokkaichi (JP); Yuji Yamada, Kuwana (JP); Ayako Mizuno, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 14/819,576

(22) Filed: Aug. 6, 2015

(65) Prior Publication Data

US 2016/0209389 A1     Jul. 21, 2016

Related U.S. Application Data (60) Provisional application No. 62/103,628, filed on Jan. 15, 2015.

(51) Int. Cl.
  *G01N 33/20* (2006.01)
  *G01N 31/00* (2006.01)

(52) U.S. Cl.
  CPC ......... *G01N 33/20* (2013.01); *G01N 31/005* (2013.01)

(58) Field of Classification Search
  CPC ...... G01N 33/20; G01N 33/00; G01N 31/005; G01N 31/00
  USPC ......................................................... 436/73
  See application file for complete search history.

(56) References Cited

U.S. PATENT DOCUMENTS

| | | | |
|---|---|---|---|
| 6,444,010 B1 | 9/2002 | Watanabe | |
| 2002/0011257 A1* | 1/2002 | Degendt | G03F 7/42 134/3 |
| 2002/0066717 A1* | 6/2002 | Verhaverbeke | C02F 1/78 216/13 |
| 2005/0208674 A1* | 9/2005 | Tokushima | H01L 21/67253 436/178 |

FOREIGN PATENT DOCUMENTS

| | | |
|---|---|---|
| JP | 5-218164 | 8/1993 |
| JP | 5-226443 | 9/1993 |
| JP | 2001-77158 | 3/2001 |
| JP | 2001-144083 | 5/2001 |
| JP | 2009-206252 | 9/2009 |
| JP | 2011-82338 | 4/2011 |
| JP | 2012-174964 | 9/2012 |
| JP | 2013-115261 | 6/2013 |

* cited by examiner

*Primary Examiner* — Christine T Mui
(74) *Attorney, Agent, or Firm* — Oblon, McClelland, Maier & Neustadt, L.L.P.

(57) ABSTRACT

A metal collection solution according to an embodiment contains 48 wt % or more of $HNO_3$, 6 wt % or less of HCl, and 5 wt % or less of HF. The metal collection solution can collect noble metals and can scan on a substrate. The metal collection solution can be used to collect the noble metals adhered to a surface of the substrate.

10 Claims, 8 Drawing Sheets

FIG. 1

| HNO3/HCl (v/v MIXTURE VOLUME RATIO) | 0:10 | 1:9 | 2:8 | 3:7 | 4:6 | 5:5 | 6:4 | 7:3 | 8:2 | 9:1 | 10:0 |
|---|---|---|---|---|---|---|---|---|---|---|---|
| NITRIC ACID | 0% | 7% | 14% | 20% | 27% | 34% | 41% | 48% | 54% | 61% | 68% |
| HYDROCHLORIC ACID | 20% | 18% | 16% | 14% | 12% | 10% | 8% | 6% | 4% | 2% | 0% |

CONCENTRATION OF ULTRAPURE NITRIC ACID STOCK SOLUTION: 68%, CONCENTRATION OF ULTRAPURE HYDROCHLORIC ACID STOCK SOLUTION: 20%

| HF CONCENTRATION | AMOUNT OF COLLECTION SOLUTION(ul) (BEFORE SCANNING) | AMOUNT OF COLLECTION SOLUTION(ul) (AFTER SCANNING) | COLLECTION RATE OF COLLECTION SOLUTION(%) |
|---|---|---|---|
| 0% | 1000 | CANNOT BE COLLECTED | - |
| 1% | 1000 | 998 | 99.8 |
| 2% | 1000 | 997 | 99.7 |
| 3% | 1000 | 998 | 99.8 |
| 4% | 1000 | 852 | 85.2 |
| 5% | 1000 | 724 | 72.4 |
| ≧6% | 1000 | CANNOT BE COLLECTED | - |

METAL COLLECTION SOLUTION AND METHOD OF ANALYZING SUBSTRATE CONTAMINATION

CROSS REFERENCE TO RELATED APPLICATION(S)

This application is based upon and claims the benefit of priority from the prior U.S. Provisional Patent Application No. 62/103,628, filed on Jan. 15, 2015, the entire contents of which are incorporated herein by reference.

FIELD

Embodiments of the present invention relates to a metal collection solution and a method of analyzing substrate contamination.

BACKGROUND

In recent years, noble metals are used in a fabrication process with miniaturization and high integration of a semiconductor device. Since contamination of a substrate due to the noble metals adversely affects properties of the semiconductor device, the analysis of the noble metals on the substrate is an important issue.

A method of analyzing substrate contamination due to metals has been used in the related arts in which a metal collection solution scans on the substrate using an automatic collection device, the metals on the substrate are collected into the metal collection solution, and the metals contained in the metal collection solution are analyzed. As the metal collection solution, for example, $HF/H_2O_2$, $HCl/H_2O_2$, or $HF/HCl/H_2O_2$ is used.

However, the above-described analysis method used in the related arts may not be used as a method of analyzing substrate contamination due to the noble metals. This is because the noble metals having high oxidation-reduction potential deprive of electrons of Si constituting the substrate and become metals of noble metals on the substrate, resulting in not being collected by the metal collection solution having relatively weak oxidation power.

Therefore, a method is proposed in which aqua regia or $HF/HNO_3$ having strong oxidation power is employed as a metal collection solution for collecting the noble metals. However, there is a problem that the aqua regia or the like may not scan on the substrate using the automatic collection device, due to low scanning property.

For this reason, when the aqua regia or the like is used as the metal collection solution, it is necessary to apply the metal collection solution onto the wide range or entire of the surface of the substrate by a manual method (by operating engineer). In addition, since the large amounts of metal collection solutions are used, it is necessary to concentrate the metal collection solution after collecting the noble metals. In addition, since the noble metals are collected by the manual method, dedicated instruments or engineers having a high degree of skill acquisition are required.

Thus, according to the analysis method using the metal collection solution of the aqua regia or the like, processes are complicated and it takes a long time for the analysis. Accordingly, it is difficult to efficiently analyze the substrate contamination due to the noble metals in this analysis method. When the substrate has a large diameter in the future, it is increasingly difficult to analyze the substrate contamination using such a method.

For this reason, there is a strong need for a metal collection solution, which can collect noble metals and can scan on a substrate, and a method of efficiently analyzing substrate contamination using such a metal collection solution.

DETAILED DESCRIPTION

Embodiments will now be explained with reference to the accompanying drawings. The present invention is not limited to the embodiments.

A metal collection solution according to an embodiment contains 48 wt % or more of $HNO_3$, 6 wt % or less of HCl, and 5 wt % or less of HF.

(Metal Collection Solution)

A metal collection solution (hereinafter, simply referred to as a "collection solution") according to an embodiment will be described with reference to FIGS. 1 to 7. The collection solution according to the invention is used to collect noble metals adhered to a surface of a silicon substrate (hereinafter, referred to as a "substrate"). The collection solution is a mixture solution of three kinds of acids obtained by adding trace amounts of HF (hydrofluoric acid) to a mixture solution of $HNO_3$ (nitric acid) and HCl (hydrochloric acid).

First, the role of each component contained in the collection solution will be described.

NOCl (nitrosyl chloride) and $Cl_2$ (chlorine) produced by a reaction of $HNO_3$ and HCl are dissolved in the collection solution according to the embodiment.

$$HNO_3 + HCl \rightarrow NOCl + Cl_2 + H_2O \quad \text{(Formula 1)}$$

It is considered that the NOCl and $Cl_2$ dissolved in the collection solution mainly have two roles. A first role is to collect noble metals in the collection solution.

The NOCl and $Cl_2$ have strong oxidation power and react with a noble metal M as indicated in the following Formula.

$$M + NOCl + Cl_2 + HCl \rightarrow H[MCl_n] + NO \quad \text{(Formula 2)}$$

By the reaction of Formula 2, the collection solution can dissolve the noble metal to collect it.

A second role is to suppress the decrease in scanning property of the collection solution. The scanning property of the collection solution will be described below.

Figure 1:
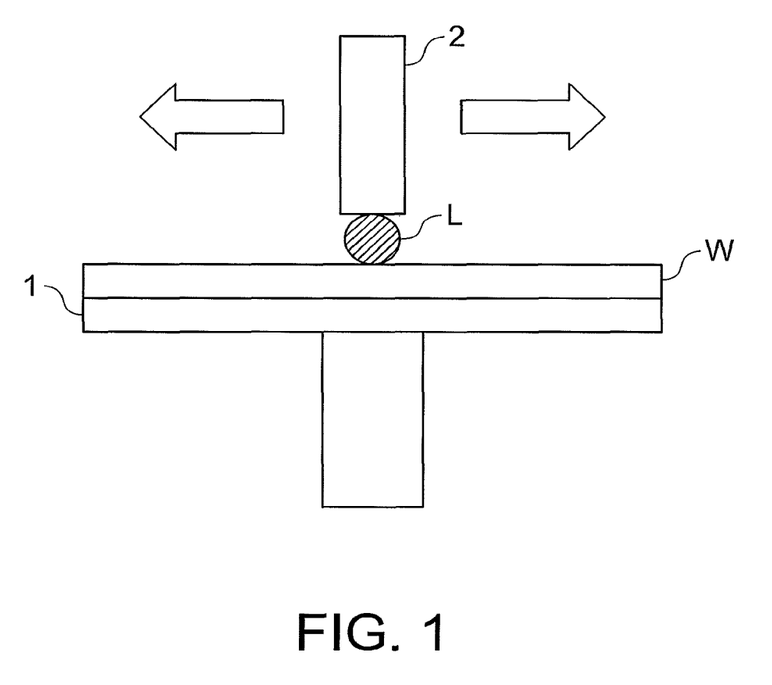
FIG. 1 is a schematic diagram illustrating a configuration of an automatic collection device.

FIG. 1 is a schematic diagram illustrating a configuration of an automatic collection device. As illustrated in FIG. 1, the automatic collection device includes a support member 1 and a nozzle 2.

The support member 1 is a table which is configured to support a lower surface of a substrate W. The nozzle 2 is configured to supply a collection solution L to a surface of the substrate W placed on the support member 1 and moves in a horizontal direction (direction indicated by an arrow in FIG. 1) while holding the collection solution L at a tip thereof. Thus, the collection solution L scans along the surface of the substrate W. The nozzle 2 collects the collection solution L after the scanning of the collection solution L. By analysis of the noble metals contained in the collection solution collected by the nozzle 2, the substrate contamination due to the noble metals is analyzed.

The above-described scanning property refers to mobility of the collection solution on the substrate. When the scanning property is high, the collection solution L moves on the substrate W while being held at the tip of the nozzle 2 with the movement of the nozzle 2. For this reason, the collection solution L is held at the tip of the nozzle 2 even after scanning on the substrate W. In this case, the automatic collection device can hold the collection solution L using the nozzle 2.

On the contrary, when the scanning property is low, the collection solution L does not keep up with the movement of the nozzle 2 and is left behind on the substrate W if the nozzle 2 moves. For this reason, if the nozzle 2 moves, the collection solution L would be away from the tip of the nozzle 2. In this case, the automatic collection device may not hold the collection solution L using the nozzle 2.

When the collection solution according to the embodiment comes in contact with the substrate, $HNO_3$ reacts with Si which constitutes the substrate as indicated in the following Formula.

$$Si + HNO_3 \rightarrow SiO_2 + NO + H_2O \quad \text{(Formula 3)}$$

When the reaction rate of Formula 3 is fast, the interaction between the collection solution and the substrate becomes stronger and thus the scanning property of the collection solution decreases. However, since the NOCl and $Cl_2$ suppress the reaction of Formula 3 in the embodiment, the decrease in the scanning property of the collection solution is suppressed.

In addition, HF contained in the collection solution plays a role of improving the scanning property of the collection solution. As described above, when the $HNO_3$ reacts with Si to produce $SiO_2$, the interaction between the collection solution and the substrate becomes stronger, and thus the scanning property decreases. However, HF reacts with $SiO_2$, which is produced by the reaction of Formula 3, as indicated by the following Formula in the present embodiment.

$$SiO_2 + HF \rightarrow H_2SiO_6 + H_2O \quad \text{(Formula 4)}$$

Since the $SiO_2$ produced on the surface of the substrate is decomposed by the reaction of Formula 4, the interaction between the collection solution and the substrate becomes weaken, and thus the scanning property of the collection solution improves.

A mixing ratio of each component in the collection solution will be described below.

The collection solution according to the present embodiment contains 48 wt % or more of $HNO_3$, 6 wt % or less of HCl, and 5 wt % or less of HF. First, the mixing ratio of $HNO_3$ and HCl will be described.

Figure 2:
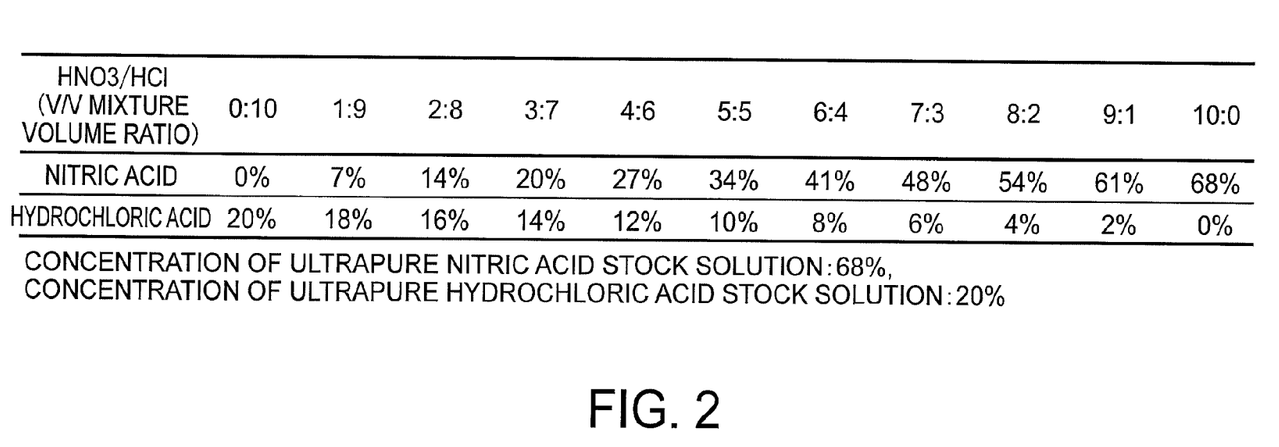
FIG. 2 is a table indicating a relation between a mixture volume ratio of $HNO_3$ to HCl and a concentration thereof.

FIG. 2 is a table indicating the relation between a mixture volume ratio (V/V) of $HNO_3$ to HCl and a concentration (wt % concentration) thereof. In FIG. 2, a stock solution of $HNO_3$ is an ultrapure nitric acid stock solution having a concentration of 68 wt %, and a stock solution of HCl is an ultrapure hydrochloric acid stock solution having a concentration of 20 wt %. As indicated in FIG. 2, for example, when the stock solutions of $HNO_3$ and HCl are mixed with each other at a mixture volume ratio of 5:5, the concentration of $HNO_3$ is 34 wt % and the concentration of HCl 10 wt %.

Figure 3:
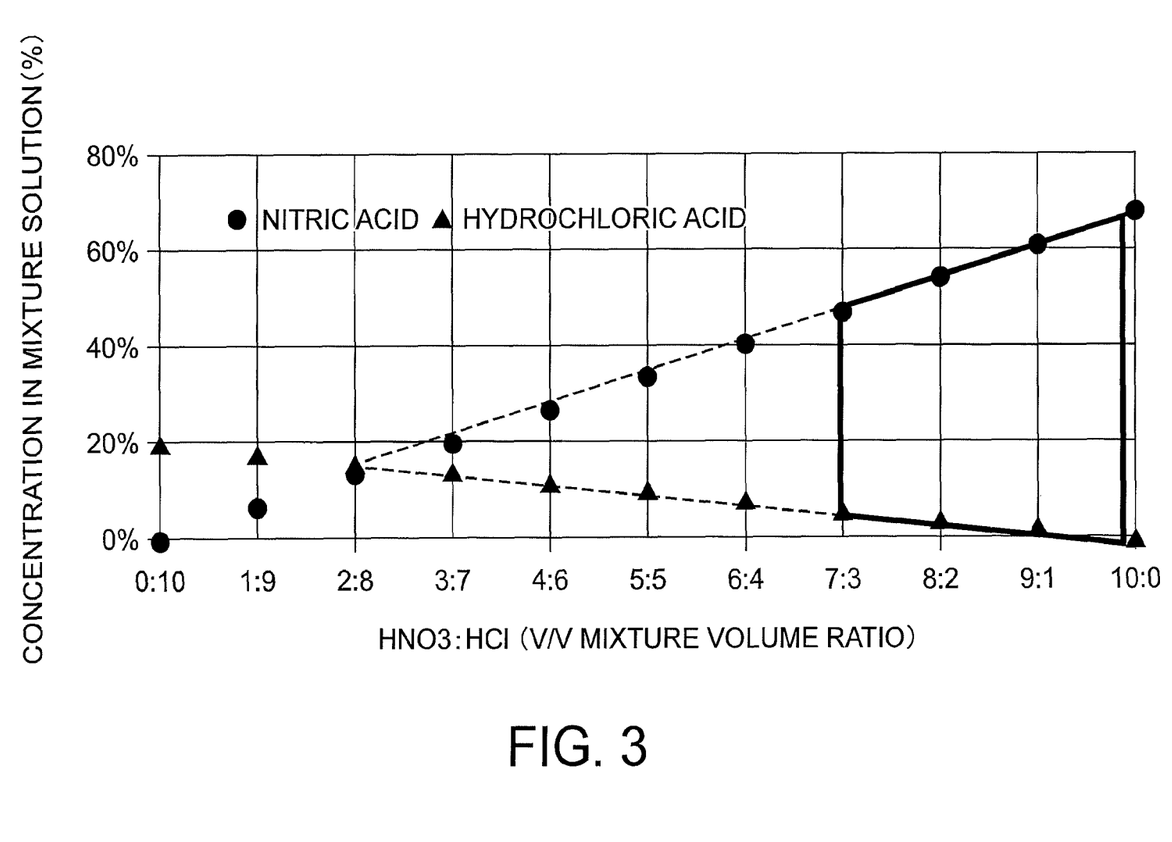
FIG. 3 is a graph indicating the relation between the mixture volume ratio of $HNO_3$ to HCl and the concentration thereof.

FIG. 3 is a graph indicating a relation between the mixture volume ratio (V/V) of $HNO_3$ to HCl and the concentration (wt % concentration) thereof. FIG. 3 corresponds to the table of FIG. 2. In FIG. 3, the concentration range of the collection solution according to the present embodiment is illustrated by a solid line.

The present inventors have measured pressure variation after the adjustment of the mixture solution with respect to the mixture solution of each mixture volume ratio indicated in FIGS. 2 and 3. As a result, the inventors find that the pressure rise after the adjustment of the mixture solution is large and the pressure rise continues for 24 hours or longer at the mixture solution in which the mixture volume ratio of $HNO_3$ to HCl is 0:10 to 6:4, that is, the mixture solution in which the concentration of $HNO_3$ is 41 wt % or less and the concentration of HCl is 8 wt % or more.

The reason of the pressure rise is that the reaction of $HNO_3$ and HCl (Formula 1) vigorously proceeds and NOCl or $Cl_2$ gets out of the mixture solution in the form of bubbles, and then the pressure of the mixture solution rises. In addition, the pressure rise proceeds for a long time to make the amount of HCl excessively large with respect to $HNO_3$ and thus to maintain the reaction of Formula 1 for a long time.

Such a mixture solution is not suitable for a collection solution to be used in an automatic collection device. This is because when bubbles of the collection solution is a lot, the collection solution leaks from the nozzle 2 due to an increase in internal pressure, resulting in difficulty of holding the collection solution.

In contrast, the inventors finds that the pressure rise after the adjustment of the mixture solution is small and the pressure rise is completed with a few hours at the mixture solution in which the mixture volume ratio of $HNO_3$ to HCl is 7:3 to 10:0, that is, the mixture solution in which the concentration of $HNO_3$ is 48 wt % or more and the concentration of HCl is 6 wt % or less.

Such a mixture solution having little bubbles and being stabilized in a short time is suitable for the collection solution to be used in the automatic collection device since the internal pressure of the nozzle 2 hardly rises. Therefore, from the viewpoint of the low internal pressure, the collection solution according to the present embodiment contains 48 wt % or more of $HNO_3$ and 6 wt % or less of HCl.

However, when the collection solution does not contain HCl (0 wt %), the reaction of Formula 1 does not occur, and the oxidation power and the scanning property of the collection solution decrease. For this reason, the collection solution contains HCl more than 0 wt %. As a result, the collection solution contains $HNO_3$ less than 68 wt %.

Accordingly, as illustrated in FIG. 3, a concentration X of the $HNO_3$ contained in the collection solution satisfies a relation of 48 wt % ≤ X < 68 wt %, and a concentration Y of the HCl contained in the collection solution satisfies a relation of 0 wt % < Y ≤ 6 wt %.

Figure 4:
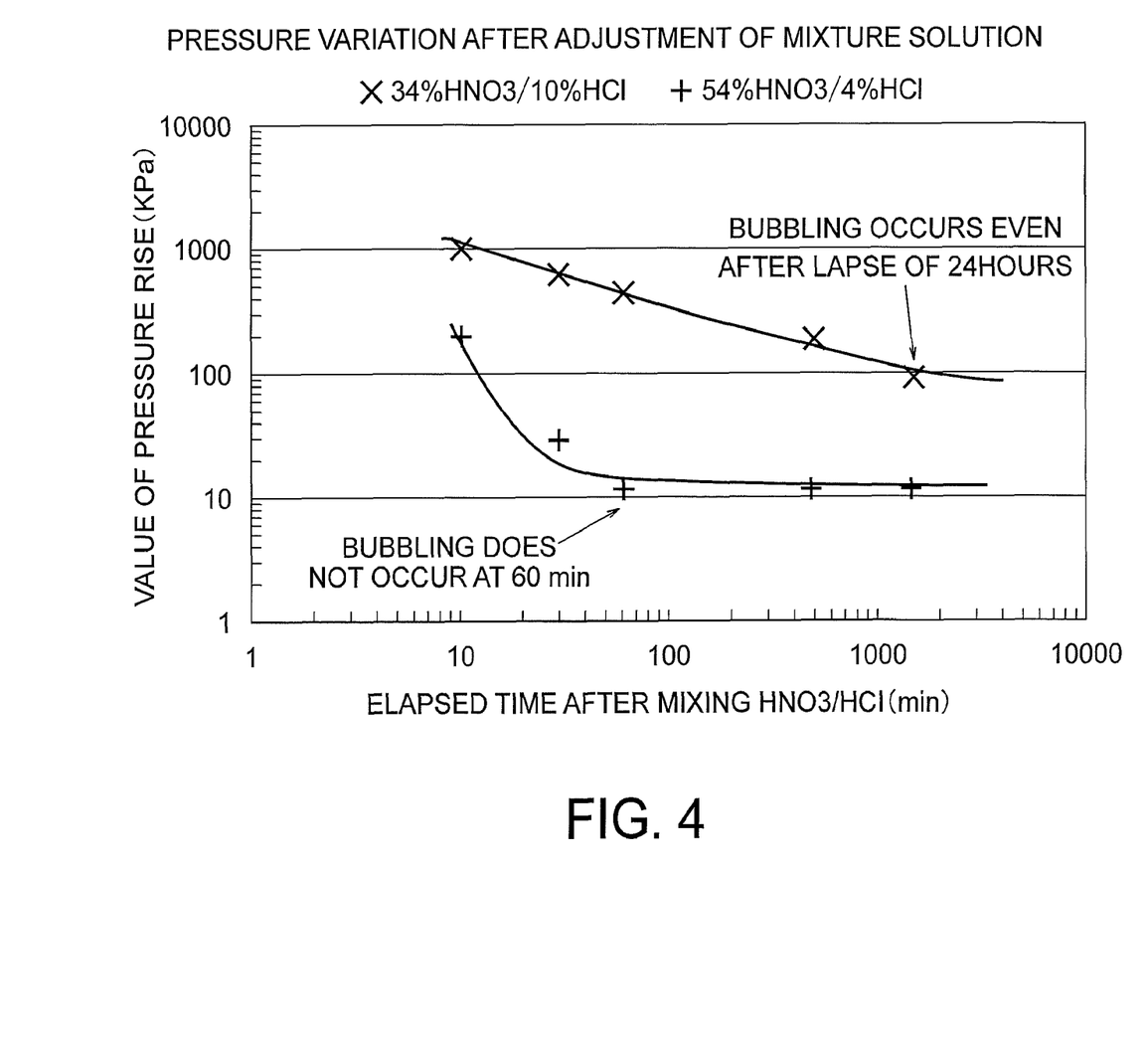
FIG. 4 is a graph illustrating an example of a measurement result of the pressure variation in the mixture solution of $HNO_3$ and HCl.

Here, FIG. 4 is a graph illustrating an example of a measurement result of the pressure variation. As illustrated in FIG. 4, with respect to a mixture solution containing 34 wt % of $HNO_3$ and 10 wt % of HCl, bubbling continues even after a lapse of 24 hours and the pressure rise is large. In contrast, with respect to a mixture solution containing 54 wt % of $HNO_3$ and 4 wt % of HCl, the bubbling is completed at about 60 minutes and the pressure rise is also small.

The mixing ratio of HF will be described below. The present inventors measured collection rates of a plurality of collection solutions containing HF of different concentrations, respectively. This experiment is performed in such a manner that: a collection solution of 1000 ul is supplied to a bare silicon substrate of ϕ 300; the substrate is scanned by the supplied collection solution; and then the collection solution is collected by the automatic collection device, thereby measuring the collected amount. In addition, a collection solution containing 50 wt % of $HNO_3$ and 3 wt % of HCl is used in this experiment.

Figure 5:
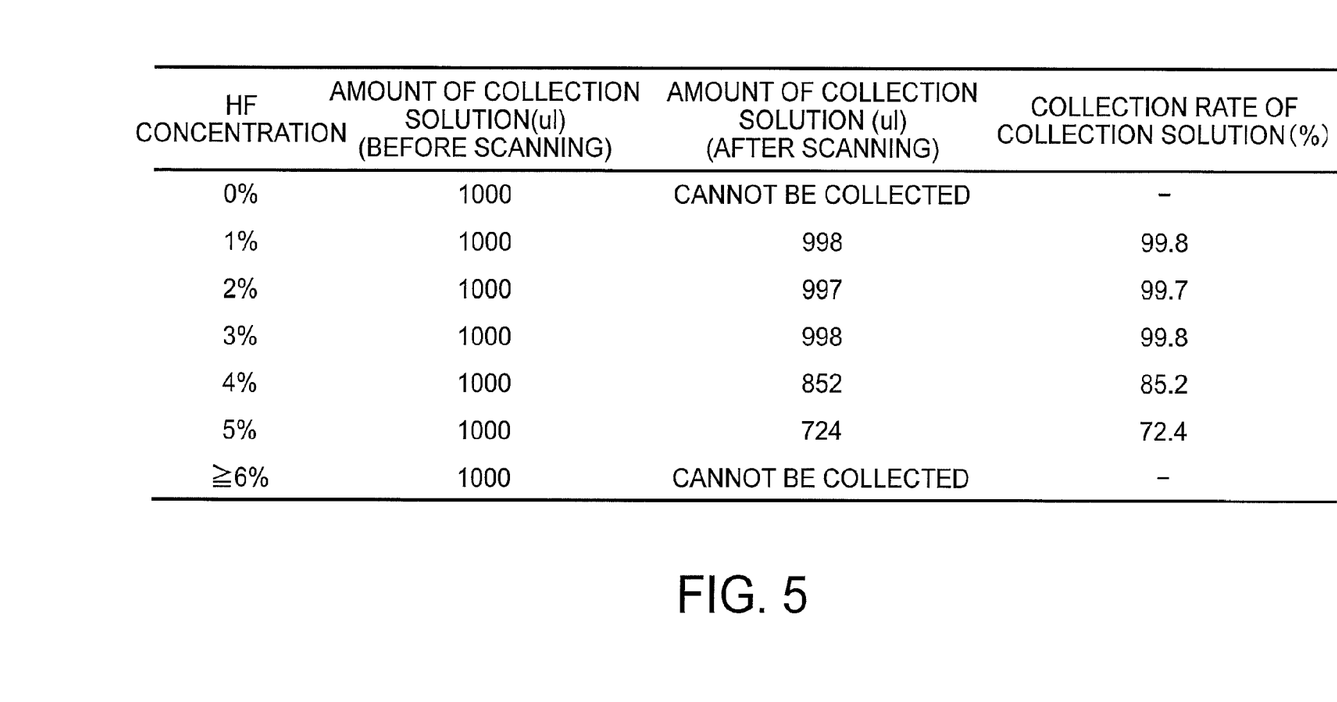
FIG. 5 is a table indicating a measurement result of a collection rate of a metal collection solution.

FIG. 5 is a table indicating a measurement result of the collected amount due to this experiment. As indicated in FIG. 5, for example, the collection rate after the scanning of a collection solution containing 1 wt % of HF is 99.8%. In contrast, a collection solution containing 6 wt % or more of HF cannot be collected.

This is because the scanning property of the collection solution decreases when the concentration of HF is too high. As described above, in the collection solution of the present embodiment, $SiO_2$ on the substrate decreases due to the reaction of Formula 4 and the scanning property improves. However, when the concentration of HF contained in the collection solution is too high, a consumption rate of $SiO_2$ due to the reaction of Formula 4 becomes faster and the reaction of Formula 3 vigorously proceeds, but rather the scanning property of the collection solution decreases.

As a result of the experiment, as indicated in FIG. 5, it is found that the scanning property of the collection solution is low and the collection solution cannot be collected by the automatic collection device when the concentration of HF is 6 wt % or more; and the scanning property of the collection solution improves and the collection solution can be collected by the automatic collection device when the concentration of HF is 5 wt % or less.

Therefore, in view of the scanning property, the collection solution according to the present embodiment contains 5 wt % or less of HF. In addition, it can be seen from FIG. 5 that the collection rate of the collection solution is 99% or more and the collection solution has high scanning property when the concentration of HF is 3 wt % or less. For this reason, the collection solution preferably contains 3 wt % or less of HF.

However, as indicated in FIG. 5, the scanning property of the collection solution decreases and the collection solution cannot be collected by the automatic collection device when the collection solution does not contain HF. This is because the scanning property is not improved due to the reaction of Formula 4. For this reason, the collection solution contains HF more than 0 wt %. Accordingly, a concentration Z of HF contained in the collection solution satisfies a relation of 0 wt % < Z ≤ 5 wt %.

As described above, the collection solution according to the present embodiment contains 48 wt % or more of $HNO_3$, 6 wt % or less of HCl, and 5 wt % or less of HF. By such a mixing ratio, the collection solution with low internal pressure has high scanning property on the substrate.

Therefore, the collection solution scans on the substrate and then can be collected using the automatic collection device. For this reason, since the scanning, collect, and analysis of the collection solution can be automatically performed by a substrate contamination analyzing apparatus having the automatic collection device, the substrate contamination can be efficiently analyzed in a short time and the substrate contamination due to noble metals can be also measured and managed online from a remote place.

In addition, since the collection solution according to the present embodiment is not necessary to be applied in a wide range of the substrate, it is possible to reduce use of the collection solution.

Figure 6:
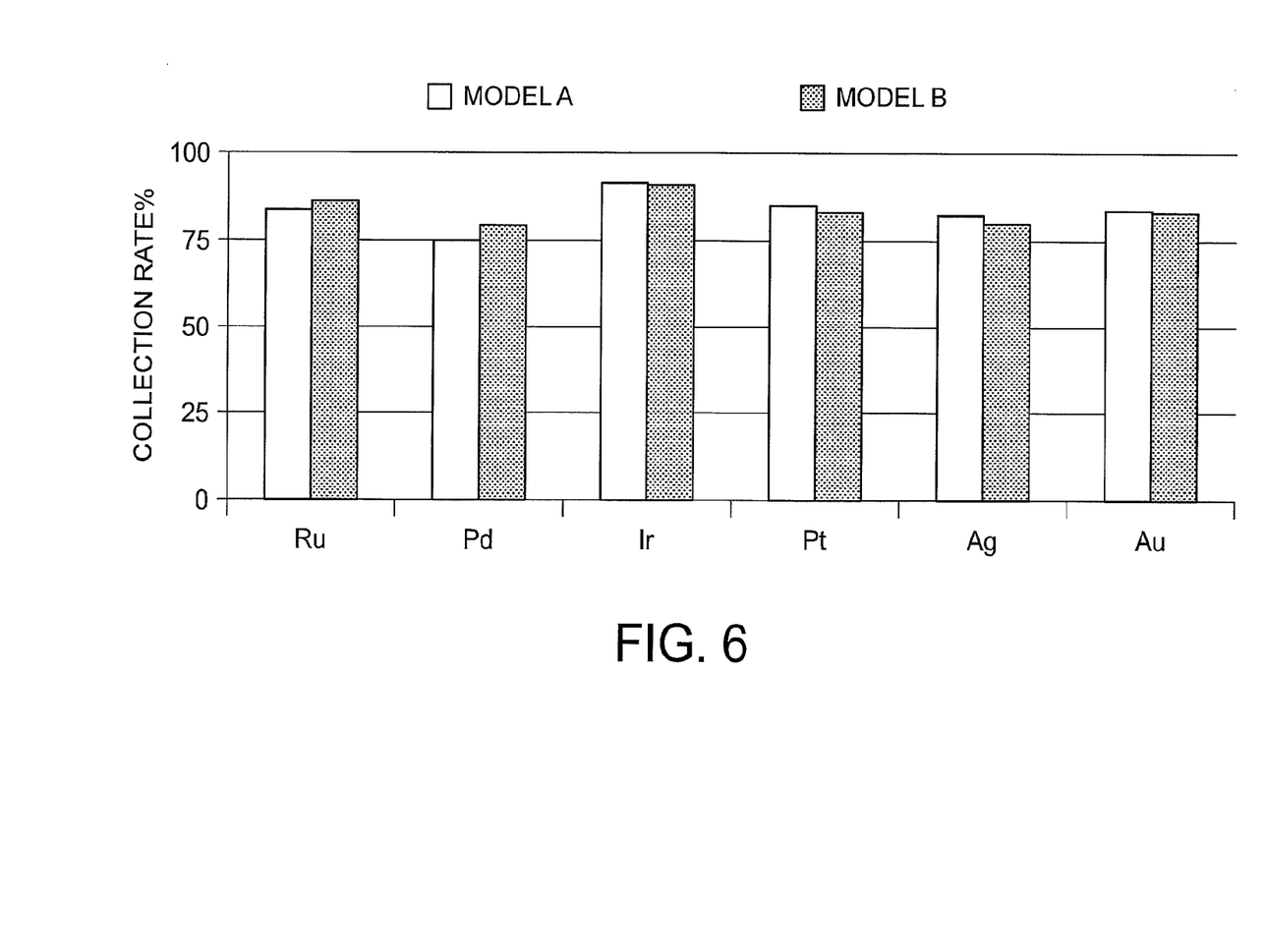
FIG. 6 is a graph illustrating a measurement result of a collection rate of noble metals.

In addition, the collection solution according to the present embodiment has a high collection rate of noble metals. Here, FIG. 6 is a graph illustrating a measurement result of a collection rate of noble metals using the collection solution according to the present embodiment. In this experiment, the collection rate of noble metals is measured in such a manner of: allowing the collection solution to scan on the forcedly contaminated substrate of ϕ 300; collecting the collection solution using the automatic collection device; and analyzing metals contained in the collected collection solution. The noble metals of which the collection rate is measured are Ru, Pd, Ir, Pt, Ag, and Au. In addition, as the collection solution according to the present embodiment, a collection solution containing 54 wt % of $HNO_3$, 3 wt % of HCl, and 1 wt % of HF is used. In addition, the experiment is performed by each of two types of automatic collection devices of models A and B.

As a result of this experiment, as illustrated in FIG. 6, it is measured by both types of automatic collection devices of models A and B that all of the noble metals described above have the high collection rate of 75% or more.

Figure 7:
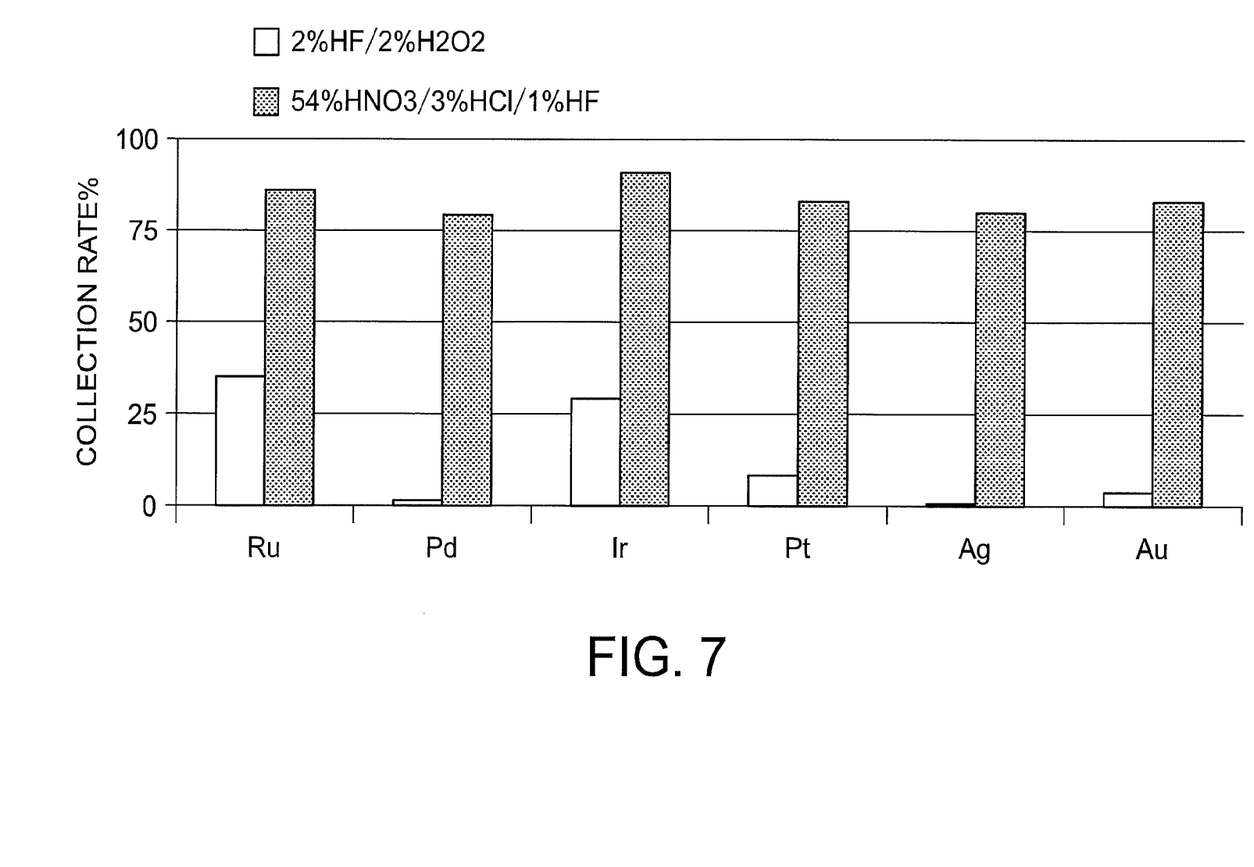
FIG. 7 is a graph illustrating a result obtained by comparing the collection rate of the noble metals measured by the metal collection solution according to the present embodiment with the collection rate of the noble metals measured by the existing metal collection solution.

FIG. 7 is a graph illustrating a result obtained by comparing the collection rate of the noble metals measured by the collection solution according to the present embodiment with the collection rate of the noble metals measured by the existing collection solution. In this experiment, the collection rate of the noble metals is measured in such a manner of: allowing the collection solution to scan on the forcedly contaminated substrate of ϕ 300; collecting the collection solution using the automatic collection device; and analyzing metals contained in the collected collection solution. The scanning of the collection solution is performed using a nozzle having a size of ϕ 10 mm on condition that a scanning speed is 10 mm/sec. and a feed pitch is 5 mm. Time required for the scanning of the collection solution is about 30 minutes.

The noble metals of which the collection rate is measured are Ru, Pd, Ir, Pt, Ag, and Au. The collection solution containing 54 wt % of $HNO_3$, 3 wt % of HCl, and 1 wt % of HF is used as the collection solution according to the present embodiment, and a collection solution containing 2 wt % of HF and 2 wt % of $H_2O_2$ is used as the existing collection solution.

As a result of this experiment, as illustrated in FIG. 7, it is found that the collection solution according to the present embodiment has a high collection rate of all of the noble metals described above as compared to the existing collection solution.

The collection solution according to the present embodiment can be also used as a collection solution for collecting metals other than the noble metals.

(Method of Analyzing Substrate Contamination)

Figure 8:
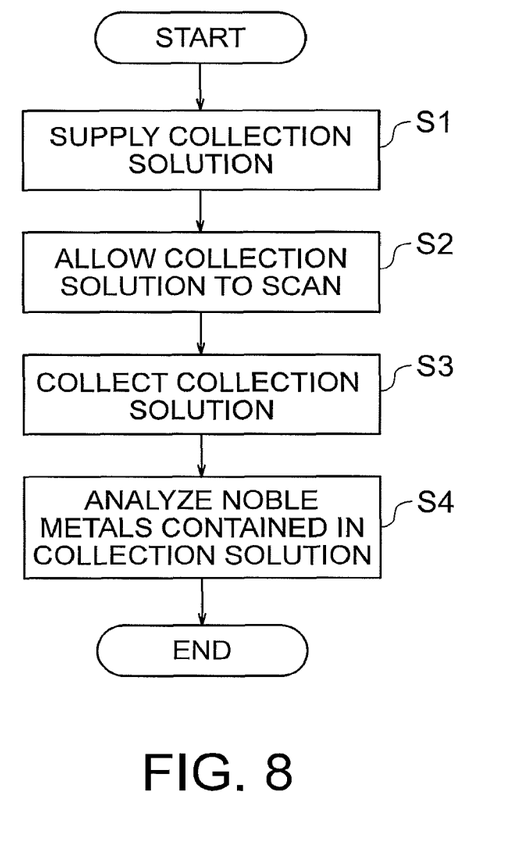
FIG. 8 is a flowchart illustrating a method of analyzing substrate contamination.

A method of analyzing substrate contamination according to the first embodiment will be described below with reference to FIG. 8. FIG. 8 is a flowchart illustrating the method of analyzing the substrate contamination according to the present embodiment.

In step S1, a collection solution is supplied onto a substrate. The collection solution is the above-described collection solution containing 48 wt % or more of $HNO_3$, 6 wt % or less of HCl, and 5 wt % or less of HF. For example, the collection solution is supplied onto the substrate from the nozzle 2 of the automatic collection device.

In step S2, the collection solution scans on the substrate. For example, the collection solution scans in such a manner that the nozzle 2 moves in the horizontal direction on the substrate while holding the collection solution at the tip. The noble metals adhered onto the substrate are collected into the collection solution by the scanning of the collection solution onto the substrate.

In step S3, the collection solution is collected. For example, the collection solution is collected in such a manner that the nozzle 2 of the automatic collection device inhales the collection solution held at the tip.

In step S4, the noble metals contained in the collection solution, which is collected, are analyzed. For example, the noble metals contained in the collection solution is analyzed using an atomic absorption spectrophotometry (AAS method) or an inductively coupled plasma mass spectrometry (ICP-MS method) by the substrate contamination analyzing apparatus including the automatic collection device. At this time, metals other than the noble metals may be analyzed.

As described above, since all of the processes in the method of analyzing the substrate contamination according to the present embodiment can be automatically executed by the substrate contamination analyzing apparatus, it is possible to efficiently analyze the substrate contamination in a short time and to also analyze and manage the substrate contamination online from a remote place.

In addition, it is possible to collect the noble metals on the substrate at a high collection rate using the collection solution according to the present embodiment. Accordingly, it is possible to perform the substrate analysis of high sensitivity.

In addition, since the small amount of the collection solution is used and a residue of Si produced by the scanning of the collection solution is small, a residue treatment process can be omitted.

The method of analyzing the substrate contamination according to the present embodiment can be applied to the analysis of the contamination of the metals and the noble metals contained in: the surface of an oxide film, a nitride film, or an oxynitride film on the substrate; the surface of a non-film (bare) substrate; and the oxide film, the nitride film, or the oxynitride film on the substrate.

Furthermore, in the case of analyzing the contamination of the metals and the noble metals contained in: the surface of the non-film (bare) substrate; and the oxide film, the nitride film, or the oxynitride film on the substrate, the surface of the substrate (alternatively, film on the substrate) may be etched by an HF vapor phase decomposition prior to the step S1.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A metal collection solution containing 48 wt % or more of $HNO_3$, 6 wt % or less of HCl, and 3 wt % or less of HF.

2. The solution according to claim 1, wherein the $HNO_3$ is contained to be 54 wt % or more.

3. The solution according to claim 1, wherein the HCl is contained to be 4 wt % or less.

4. A method of analyzing substrate contamination, comprising:
   scanning on a substrate using a metal collection solution containing 48 wt % or more of $HNO_3$, 6 wt % or less of HCl, and 3 wt % or less of HF;
   collecting the metal collection solution; and
   analyzing metals contained in the metal collection solution which is collected.

5. The method according to claim 4, wherein a surface of the substrate is subjected to phase decomposition prior to the scanning.

6. The method according to claim 4, wherein the analyzing is performed by an atomic absorption spectrophotometry or an inductively coupled plasma mass spectrometry.

7. The method according to claim 4, wherein the substrate is a silicon substrate.

8. The method according to claim 4, wherein the metals contained in the metal collection solution are noble metals.

9. The method according to claim 4, wherein the metal collection solution contains the $HNO_3$ to be 54 wt % or more.

10. The method according to claim 4, wherein the metal collection solution contains the HCl to be 4 wt % or less.

* * * * *